United States Patent [19]
Kain et al.

[11] Patent Number: 5,646,411
[45] Date of Patent: Jul. 8, 1997

[54] FLUORESCENCE IMAGING SYSTEM COMPATIBLE WITH MACRO AND MICRO SCANNING OBJECTIVES

[75] Inventors: Robert C. Kain, San Jose, Calif.; Christopher C. Alexay, Walpole, N.H.

[73] Assignee: Molecular Dynamics, Inc., Sunnyvale, Calif.

[21] Appl. No.: 595,355

[22] Filed: Feb. 1, 1996

[51] Int. Cl.$^6$ ................................................. G01N 21/64
[52] U.S. Cl. ...................................................... 250/458.1
[58] Field of Search ........................................... 250/458.1

[56] References Cited

U.S. PATENT DOCUMENTS

| | | | |
|---|---|---|---|
| 4,284,897 | 8/1981 | Sawamura et al. | 250/461 B |
| 5,022,757 | 6/1991 | Modell | 356/318 |
| 5,091,652 | 2/1992 | Mathies et al. | 250/458.1 |
| 5,192,980 | 3/1993 | Dixon et al. | 356/326 |
| 5,260,578 | 11/1993 | Bliton et al. | 250/461.1 |
| 5,296,700 | 3/1994 | Kumagai | 250/216 |
| 5,381,224 | 1/1995 | Dixon et al. | 356/72 |
| 5,504,336 | 4/1996 | Noguchi | 250/458.1 |

OTHER PUBLICATIONS

Shoemaker, Richard L., et al., "An Ultrafast Laser Scanner Microscope for Digital Imaging Analysis," *IEEE Transactions on Biomedical Engineering*, vol. BME–29, No. 2, Feb. 1982, pp. 82–91.

*Primary Examiner*—Constantine Hannaher
*Attorney, Agent, or Firm*—Thomas Schneck

[57] ABSTRACT

A coaxial illumination and collection laser scanning system provides substantially uniform detection sensitivity across the field of view of an objective lens by reducing lateral chromatic aberrations at the expense of amplifying axial chromatic aberrations. Axial chromatic aberrations in the system are removed in the path of a retro-beam. A laser is in optical communication with the objective lens. The laser produces a collimated beam of coherent light that is directed by a scanner through the objective lens to illuminate a raster of spots on the sample's surface, thereby stimulating a series of small regions of the sample to emit light. The system may be used as a confocal or non-confocal imaging system. Alternatively, the system may be employed for reflection imaging of the laser beam. In a second embodiment, a plurality of lasers are provided, each of which emits a wavelength different from the remaining lasers. Each of the plurality of lasers are in optical communication with a common beam expander providing the incident beam with a plurality of wavelengths of light. The common beam expander has optical properties that introduce axial chromatic aberrations to cancel axial chromatic aberrations introduced by the objective lens, with respect to the incident beam.

42 Claims, 7 Drawing Sheets

FLUORESCENCE IMAGING SYSTEM COMPATIBLE WITH MACRO AND MICRO SCANNING OBJECTIVES

TECHNICAL FIELD

The present invention relates to laser scanning imaging systems, particularly for use in fluorescence imaging.

BACKGROUND ART

Fluorescence microscopy is often used in the fields of molecular biology, biochemistry and other life sciences. One such use is in identifying a specific antigen using antibodies. Antibodies are proteins produced by vertebrates as a defense against infection. They are made of millions of different forms, each having a different binding site and specifically recognizing the antigen that induces its production. To identify an antigen, a sample of cells is provided that contains specific antibodies coupled to a fluorescent dye. The cells are then assessed for their fluorescence. Taking advantage of the precise antigen specificity of antibodies, the cells having fluorescent properties are known to contain a specific antigen.

Originally, the fluorescence of cells was assessed manually by visual inspection, using conventional microscopy. This proved time-consuming and costly. The need for high-speed automated systems became manifest. Many high-speed imaging systems, such as confocal microscopes, are available for assaying cell samples. The illumination and collection optics, along with their relative geometry, determine in large part the parameters of the other system elements.

A prior art high-speed imaging system is shown in FIG. 1 and includes an F-Θ objective 10 positioned above a sample 11 so that the surfaces of the objective are perpendicular to the sample's normal. A laser light source 12 produces a beam 13. The objective 10 directs the beam 13 to illuminate a spot on the sample's surface. An oscillating reflective surface 14 is disposed at the pupil 15 of the system, between the light source 12 and the objective 10, to deflect the beam 13 back and forth along one axis. The sample is placed on a table to move the sample in a direction perpendicular to the first scan direction, thereby resulting in a two dimensional scan pattern on the sample's surface. The objective is not designed for coaxial collection resulting in light reflected from the sample surface being collected by a condenser assembly 16 that is separate and apart from the objective. Such a geometry results in increased system footprint, increased optical complexity and a limitation of solid angle collection. The collected light is then imaged on a photo-detector 17. The design of a classical F-Θ lens is primarily for monochromatic illumination. As a result, such lenses lack good polychromatic performance. Therefore, the objective 10 manifests lateral and axial chromatic aberrations over a broad band of wavelengths.

A prior art high-speed imaging system, similar to that described with respect to FIG. 1, is disclosed by Richard L. Shoemaker et al., in "An Ultrafast Laser Scanner Microscope for Digital Imaging Analysis", *IEEE Transactions on Biomedical Engineering*, Vol. BME-29, No. 2, February 1982, pp. 82–91. The principal difference between these two systems concerns the scanning device. Instead of a galvanometric scanner, Shoemaker et al. require the use of a rotating polygon mirror to scan the spot over the sample's surface.

Another prior art high-speed imaging system is disclosed in U.S. Pat. No. 4,284,897 by Sawamura et al., in which laser light is reflected through two galvanometric mirrors and one dichroic mirror to direct a beam through an objective and illuminate a spot on a sample's surface. The galvanometric mirrors are swung in appropriate directions to allow the spot to scan over the entire surface of the sample. In response to the illuminating spot, the sample emits fluorescence light. The objective, serving as a condenser lens, transmits the light back through a first dichroic mirror. Positioned behind the first dichroic mirror is a second dichroic mirror that splits the fluorescent light into a light produced by a first probe at a first wavelength and light produced by a second probe at a second wavelength. The first and second wavelengths are transmitted to respective photo-detectors.

U.S. Pat. No. 5,296,700 to Kumagai discloses a fluorescent confocal microscope which includes, in pertinent part, an intermediary optical system disposed between a pair of scan mirrors and an objective optical system. The intermediary optical system is designed to cancel chromatic aberrations of magnification introduced by the objective optical system.

U.S. Pat. No. 5,260,578 to Bliton et al. discloses a scanning confocal microscope which includes, in pertinent part, two beam sources. One beam source produces ultra violet light. One beam source produces visible light. An optical assembly is included in the common optical train to correct chromatically induced scanning errors.

U.S. Pat. No. 5,381,224 by Dixon et al. discloses a scanning laser imaging system which allows simultaneous confocal and non-confocal imaging of reflected light. The system includes, in pertinent part, a laser producing a beam which traverses a beam expander and impinges upon a single mirror disposed in an optical axis, which is defined by an objective lens. The objective lens directs the beam onto a sample, which is disposed upon a moveable stage. The mirror scans the beam along a first direction, and the stage moves the sample along a second direction, transverse to the first direction. In this manner, the beam scans across the sample in two directions. Disposed between the objective and the sample is a beam splitter designed to collect light emitted from the sample. The beam splitter directs a portion of light emitted from the sample onto a condenser lens, which in turn directs it onto a non-confocal detector. A portion of the light collected by the beam splitter is directed along the same path as the beam, but in an opposite direction, forming a retro-beam. The retro-beam impinges upon a second beam splitter, positioned between the scan mirror and the laser. The second beam splitter directs the light onto a focusing lens. The focusing lens is positioned proximate to a field stop, having an aperture. The aperture is confocal to the light emitted from the sample and selectively restricts light in the retro-beam from reaching the detector. Light traversing the aperture impinges upon a confocal detector.

A disadvantage of the prior art systems is that additional optics are required to correct optical aberrations over a scan field and to efficiently collect light emitted from a sample, thereby increasing the systems' cost and size.

What is needed, therefore, is to provide a high-speed, low cost, laser scanning system that will provide point by point image of a sample on both a micro and macro scale.

A further need exists to provide an imaging system of a substantially smaller size than the prior art systems that affords a larger scan field than existing coaxial illumination and collection systems.

SUMMARY OF THE INVENTION

Provided is a coaxial illumination and collection laser scanning system designed to provide substantially uniform detection sensitivity across a planar field of view by reducing lateral chromatic aberrations and allowing a predetermined amount of axial chromatic aberrations at the objective lens and removing the axial chromatic aberrations using another lens already existing in the system. A laser is in optical communication with the objective lens. The laser produces a collimated beam of coherent light that is directed through the objective lens to illuminate a spot on a sample, thereby stimulating a small region of the sample to emit light. The objective lens also serves as a condenser and collects the light emitted by the sample. The objective lens is designed with correction for lateral chromatic aberrations and without correction for axial chromatic aberrations. The objective lens directs the collected light back along the identical path traveled by the incident beam, but in an opposite direction. A wavelength-discriminating dichroic filter is placed along the optical axis between the laser and the objective lens to separate the emitted light from the incident beam, a focusing lens directs the collected light onto a photo-detector. The photo-detector produces a signal in response to the emitted light sensed, representing the sample emitting the light. The focusing lens is a doublet lens that uses two elements in order to keep a constant focal length with different wavelengths of light. The doublet lens is disposed in the path of a retro-beam and is optically designed to introduce axial chromatic aberrations necessary to correct for axial chromatic aberrations introduced elsewhere in the system, e.g., by the objective lens. To scan over the entire sample, a two dimensional scanning device having a reflecting element is disposed in the path of the incident beam. A display device is provided and synchronized with the scanning device to reproduce an image of the sample.

In a second embodiment, a plurality of lasers are provided, each of which emits one or more wavelengths different from the remaining lasers. Each of the plurality of lasers are in optical communication with a common beam expander providing the incident beam with a plurality of wavelengths of light. The common beam expander has optical properties that introduce axial chromatic aberrations to cancel axial chromatic aberrations introduced by the objective lens, with respect to the incident beam.

BEST MODE FOR CARRYING OUT THE INVENTION

Figure 2:
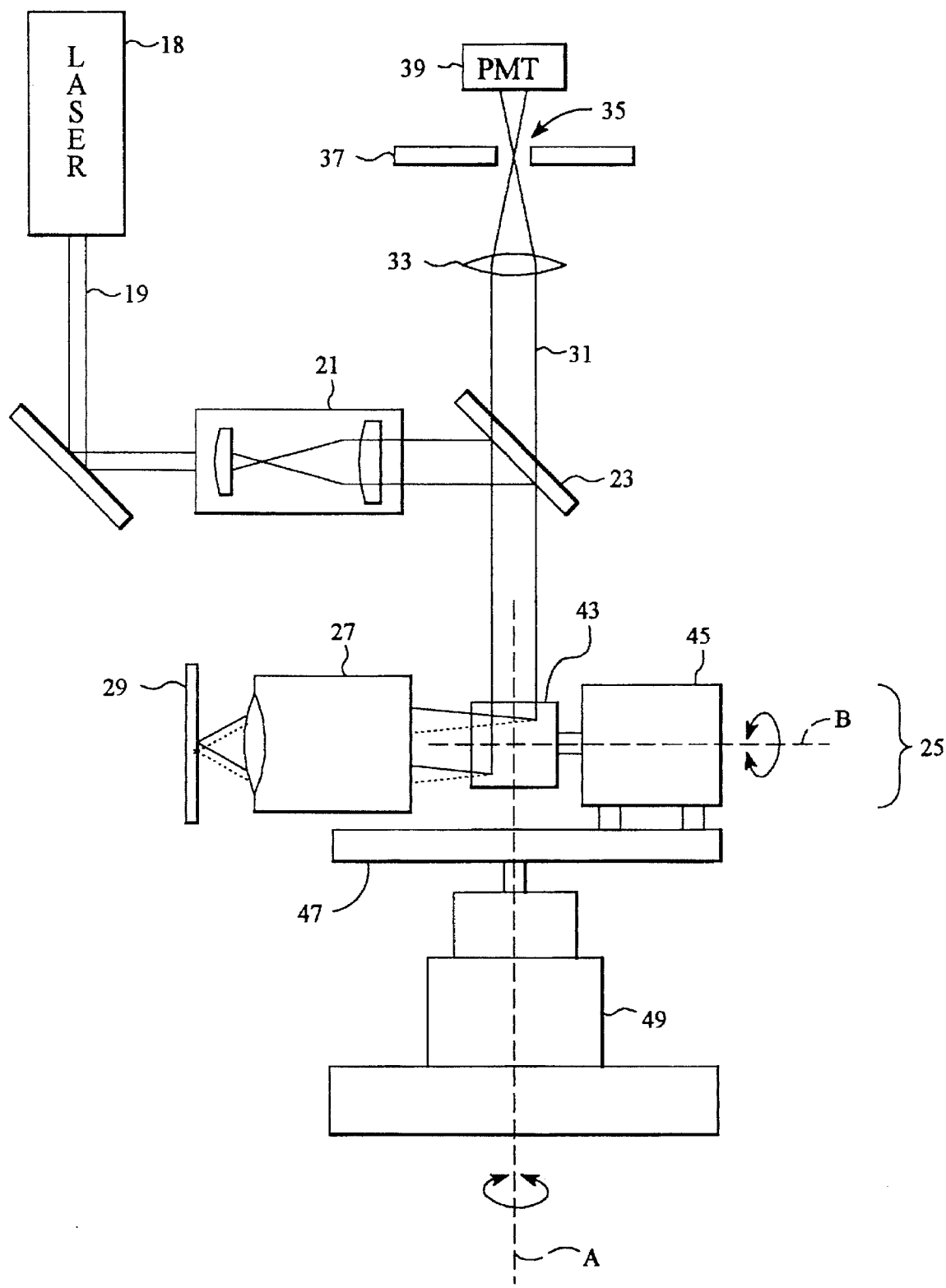
FIG. 2 is a side view of optical components of the present invention.

FIG. 2 shows a light source 18 producing an excitation/incident beam 19 of light. Beam 19 is directed through an excitation filter 20 to reduce unwanted wavelengths in the incident beam 19. Upon exiting the excitation filter 20, beam 19 impinges upon a beam expander 21 and then a beam splitter 23. Beam splitter 23 directs beam 19 onto a two dimensional scanning device 25. Two dimensional scanning device 25 directs beam 19 through an objective lens 27. Objective lens 27 directs beam 19 to illuminate a spot (not shown) on a sample 29, thereby stimulating a small region of sample 29 to emit light. Typically, the light emitted by sample 29 is fluorescent. Objective lens 27, acting as a condenser, collects the fluorescent light, forms a retro-beam 31 and directs retro-beam 31 along an identical path of incident beam 19, but in an opposite direction. Retro-beam 31 passes through a pupil stop 32, consisting of a spatial filter with an aperture. After exiting pupil stop 32, retro-beam 31 impinges upon beam splitter 23. Beam splitter 23 separates fluorescent light from the laser light and directs retro-beam 31 onto a focusing lens 33 via band pass filter 34. Focusing lens 33 directs retro-beam 31 onto a transmissive aperture 35 of a spatial filter 37, thereby causing retro-beam 31 to impinge upon a photodetector 39.

It is preferred that light source 18 is a laser producing a collimated beam of coherent light. It is possible, however, to use a non-coherent light source optically coupled to collimating optics to create an incident light beam, e.g., a light emitting diode. If a non-coherent light source, such as an LED, is employed, a pinhole and a collimating lens are disposed in front of the LED to create a collimated excitation/incident beam capable of being focused to a small spot. Band pass filter 34 typically rejects the excitation wavelengths while transmitting longer wavelengths.

Beam splitter 23 may be any known in the art, so long as it is capable of separating the light of the incident beam from the light of the retro-beam. For example, beam splitter 23 may be a dichroic filter or a 50% beam splitter. Alternatively, a polarization sensitive beam splitter may be used to achieve separation of beams 19 and 31. This embodiment could include a ¼ waveplate positioned between the beam splitter and the objective. This would cause beam 19 exiting the ¼ waveplate to be circularly polarized. Also, the separating means may be a fresnel reflector. Sample 29 is illuminated point by point, scanning the spot in a raster scan fashion over the entire area of sample 29.

Any scanning mechanism that provides a two dimensional scan may be used, e.g., a rotating polygonal mirror, rotating holographic scanner, or oscillating prisms. Also, an acousto-optic deflector or a penta-prism scanning deflector may be employed. The preferred embodiment, however, is to employ a scanning system having one beam reflecting element 43 in the path of the incident beam which is pivotable about two perpendicular axes. Reflecting element 43 is a planar mirror, but this is not essential. The mirror may be concave or convex. Refractive or diffractive deflecting elements may also be used as reflecting element 43. Mirror 43 is pivotable about axis A. Mirror 43 may be moved by any means known in the art, such as motor 45, but is typically a galvanometer mirror. Mirror 43 and motor 45 rest atop a moveable platform 47 that is rotated by a stepper motor 49. Stepper motor 49 moves platform 47 to pivot mirror 43 about axis B, which is orthogonal to axis A.

Figure 3:
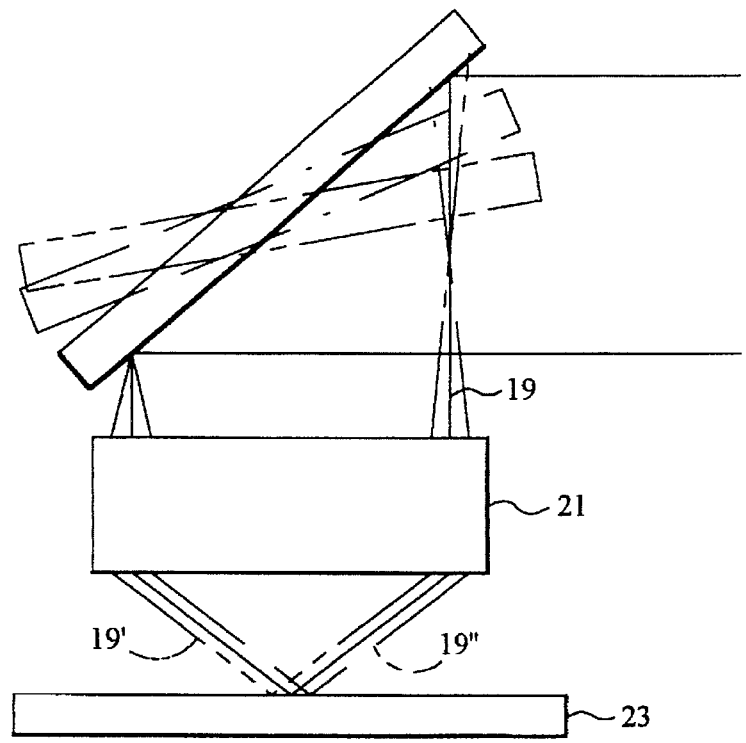
FIG. 3 is a detailed view of a scanning beam passing through the objective shown in FIG. 2.

Referring to FIG. 3, objective lens 27 typically forms an external pupil of the system and affords coaxial illumination and collection. To maximize collection efficiency, it is preferred that objective lens 27 have a large numerical aperture. With respect to incident beam 19, objective lens 27 is afocal in the image plane. Objective lens 27 is typically telecentric, or near telecentric. The telecentricity of objective lens 27 results in sample 29's surface always lying at a right angle with respect to the chief ray of incident beam 19, exiting objective lens 27. With respect to incident beam 19, the objective plane is proximate to sample 29. Beam 19 is shown entering objective lens 27 at three different positions, with beam 19 having a different angle of incidence at each position. Regardless of beam 19's angle of incidence on objective lens 27, the chief ray of beam 19 exiting objective lens 27 is orthogonal to sample 29's surface. One advantage of having this telecentric objective is that it renders the system magnification relatively insensitive to errors in focus position. In addition, objective lens 27 must be designed to operate over a broad band of wavelengths of light, e.g., the primary wavelength plus approximately 200 nm, or greater. This allows objective lens 27 to operate with lasers of various wavelengths and to collect light from a wide variety of fluorochromes.

Figure 4:
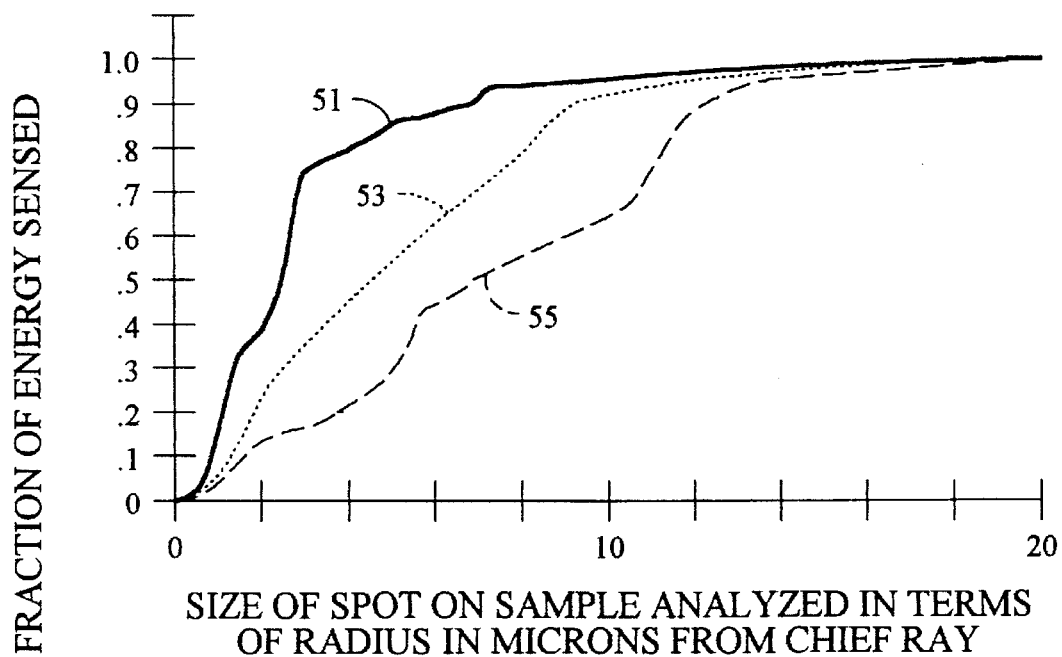
FIG. 4 is a graph showing an amount of optical energy impinging upon a detector disposed in an image plane using a common microscope system.
Figure 5:
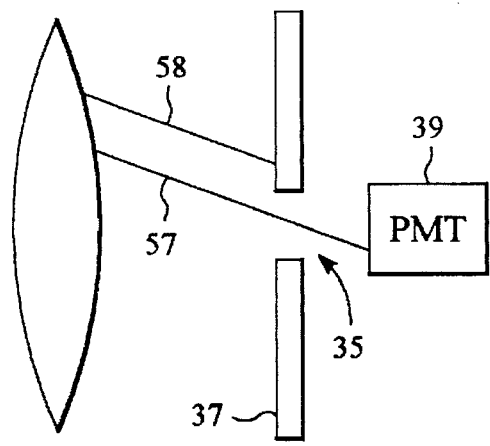
FIG. 5 is a schematic view showing the effects of lateral chromatic aberrations.

An important aspect of the system is to reduce an amount of optical loss in the field of view due to chromatic aberrations, which reduces the detection sensitivity of the system. FIG. 4 shows the relationship between field position and the relative detection sensitivity of a system not being corrected for lateral chromatic aberrations, as a function of the fraction of optical energy sensed versus size of the spot impinging upon sample 29. The amount of light detected on the optical axis 51, as defined by an objective lens, is substantially greater than the amount of light detected at a half field position 53. The lowest amount of light detected was at a full field 55 position, with the field of view defined by the objective lens. Lateral chromatic aberrations increase at larger field angles. The non-uniformity of light detected across the field of view of the lens in the system is typically a result of lateral chromatic aberrations and other field degradations such as coma. Referring to FIGS. 5 and 2, lateral chromatic aberrations may cause a reduction in detection sensitivity by allowing, e.g., green wavelengths 57 of light to pass through aperture 35 while causing longer yellow wavelengths 58 to be blocked by field stop 37.

To avoid the problems associated with lateral chromatic aberrations, it is preferred that objective lens 27 correct for all lateral chromatic aberrations in the scanning system. This may be accomplished by reducing the field of view of the objective. However, there are advantages in providing objective lens 27 with a large field of view. For example, a large (macro) field of view is useful for scanning large arrays of samples, e.g., planar field arrays containing up to a million specimens. Nonetheless, the increased field of view exacerbates the problems with lateral chromatic aberrations, because there is increasing difficulty in correcting lateral chromatic aberrations as the lens' field of view increases. The macro field of view makes lateral chromatic aberrations more pronounced, thereby making it more difficult to provide a uniform resolution across the field.

Considering the aforementioned concepts, the parameters for two implementations of objective lens 27 are as follows:

TABLE 1

|  | Micro Objective | Macro Objective |
| --- | --- | --- |
| Scan Area (diagonal) | 1 mm | 1 cm |
| Resolution | 0.6 µm | 10 µm |
| Numerical Aperture | 0.75 | 0.25 |
| Intensity Uniformity | 95% | 95% |
| Spatial Uniformity | 98% | 98% |
| Polychromatic Range | 500–750 nm | 500–750 nm |
| Thru focus sensitivity | 1% (signal change over 20 µm) | 1% (signal change over 100 µm) |
| Field Flatness Variation | +/−10 µm | +/−20 µm |
| Working Distance | 3 mm | 3.5 mm |

As can be seen above, the micro and macro objectives described may allow the system to provide between 0.6 to 20 µm resolution.

Figure 6:
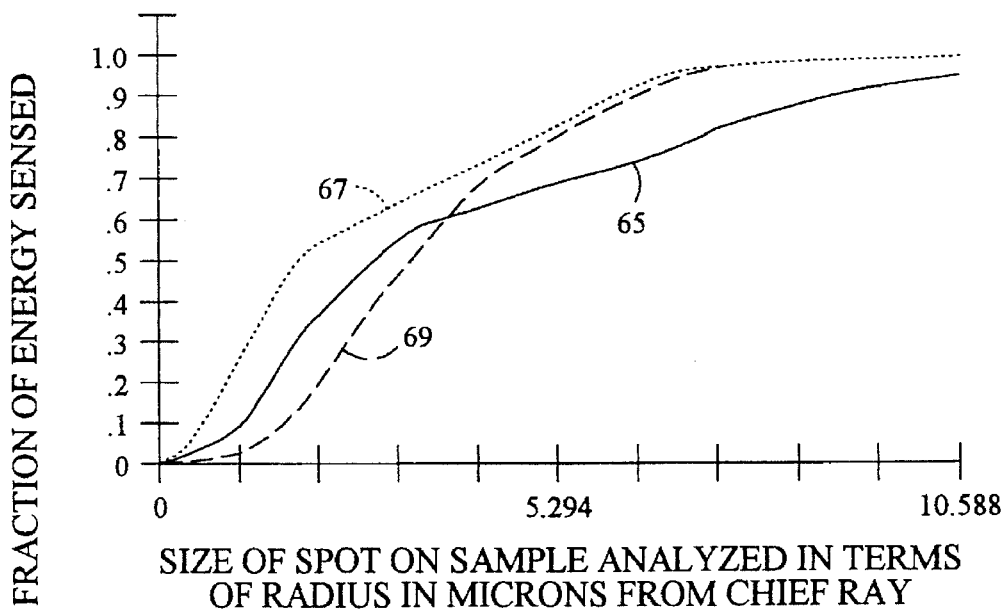
FIG. 6 is a graph showing an amount of optical energy impinging upon a detector in an image plane employing a large field objective lens of the present invention.
Figure 7:
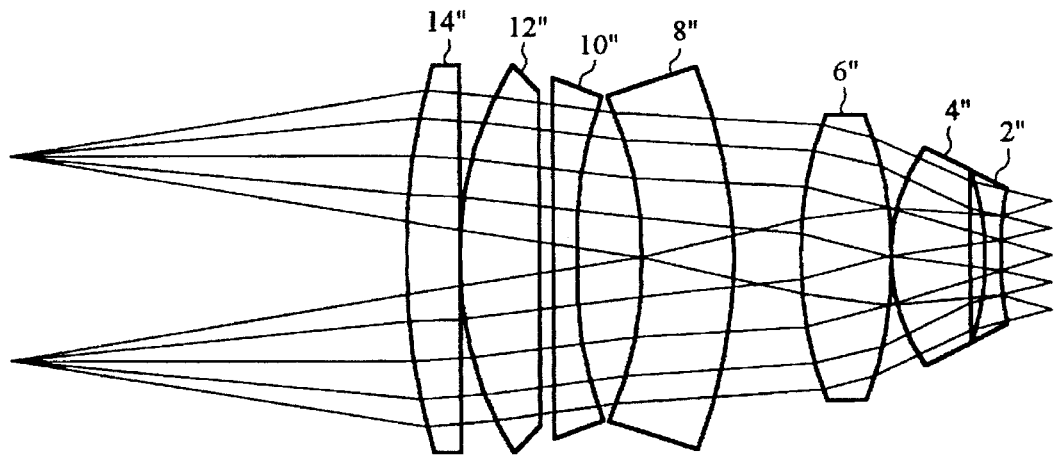
FIG. 7 is a schematic view of optical elements which comprise a large field objective lens of the present invention.

FIG. 6 shows a reduction in lateral chromatic aberrations of the macro objective lens which is achieved at the expense of amplifying axial chromatic aberrations. The increased axial chromatic aberrations are shown by the amount of light detected, at the 3 µm position, being substantially less than that shown in FIG. 4. Specifically, sensed by detector is approximately 40% of the on axis light 65 impinging upon sample 29, 3 µm from the chief ray. In FIG. 4, the amount of on axis light 51 detected 3 µm from the chief ray was nearly 80%. Nonetheless, the overall effect of lateral chromatic aberrations is shown to be substantially reduced. This is demonstrated by the amount of light detected for any given spot size being substantially the same for light at the on axis 65, half field light 67 and full field 69 positions, i.e., there exists substantial uniformity of detection sensitivity across the field of view of the macro objective lens. Additionally, FIG. 6 shows that at 10 µm from the chief ray, collection from all field points is greater than 90%. FIG. 7 shows the optical elements of the macro objective lens, and the specifications are as follows:

TABLE 2

| MACRO OBJECTIVE LENS | | | | |
| --- | --- | --- | --- | --- |
| Surface | Radius (mm) | Thickness (mm) | Material | Aperture (mm) |
| STO |  | 27.67 |  |  |
| 2" | 29.95 | 3.89 | Schott_ SK14 | 24 |
| 3 | 224.24 | 0.20 | air | 24 |
| 4" | 19.85 | 5.21 | SK14 | 24 |
| 5 | 136.67 | 0.65 | air | 20 |
| 6" | 134.23 | 2.10 | SF11 | 22 |
| 7 | 24.80 | 3.84 | air | 18 |
| 8" | −28.59 | 6.44 | SF5 | 18 |
| 9 | −60.20 | 4.86 | air | 22 |
| 10" | 27.86 | 5.73 | SK14 | 18.6 |
| 11 | −36.27 | 0.24 | air | 18.6 |
| 12" | 11.40 | 5.02 | SK14 | 14 |
| 13 | 88.81 | 0.69 | air | 11.6 |
| 14" | −33.76 | 1.32 | SF11 | 11.6 |
| 15 | 11.90 | 3.69 | air | 9 |

The aforementioned lens parameters and specifications are merely exemplary. The lens design may be adjusted to provide larger and smaller fields, as desired. This may be achieved by modifying lens radii, thickness, glass type, etc. Lenses with vastly different parameters may be designed to afford optimum performance at other resolutions and field sizes. Additionally, lenses could be designed for the same resolution and field size, as the aforementioned lenses, while satisfying different parameters, e.g., working distance and field flatness.

Figure 1:
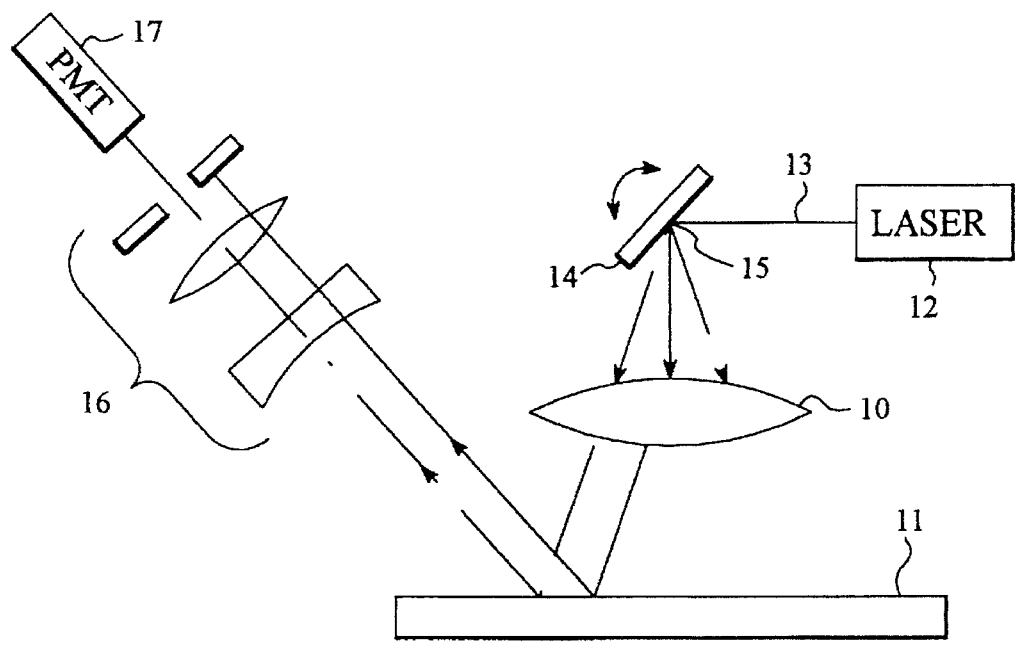
FIG. 1 is a simplified side view of a laser scanning microscope of the prior art.
Figure 8:
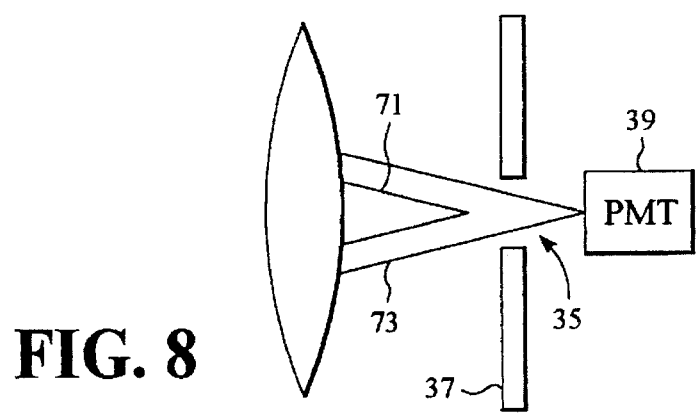
FIG. 8 is a schematic view of optical elements showing the effects of axial chromatic aberrations.

Referring to FIG. 8, similar to lateral chromatic aberrations, axial chromatic aberrations reduce the detection sensitivity of the system by having the focal length of a lens being wavelength dependent. For example, green wavelengths 71 of light focus before impinging upon detector 39, while the longer yellow wavelengths 73 of light are sensed by detector 39. Unlike lateral chromatic aberrations, however, axial chromatic aberrations do not change with the field position. Thus, the axial chromatic aberrations introduced by objective lens 27 may be kept constant, while correcting for lateral chromatic aberrations. Referring again to FIG. 1, because incident beam 19 is monochromatic, there is no need to correct axial aberrations in the incident path. Rather, axial chromatic aberrations may be corrected in the return (retro) path. It is preferred that focusing lens 33 corrects, or removes, all axial chromatic aberrations in the system. This allows manufacturing a less expensive objective lens 27, because correcting for both axial and lateral chromatic aberrations in a single lens greatly increases costs. In addition, the size/foot print of the system is kept to a minimum. As focusing lens 33 is necessary to condense retro-beam 31 onto aperture 35, no additional optics are included to reduce axial aberrations. Typically, focusing lens 33 is a doublet having the optical properties necessary to correct axial chromatic aberrations of the system. Focusing lens 33 could be composed of binary elements or any other design known in the art which focuses a beam and corrects axial chromatic aberrations.

Figure 9:
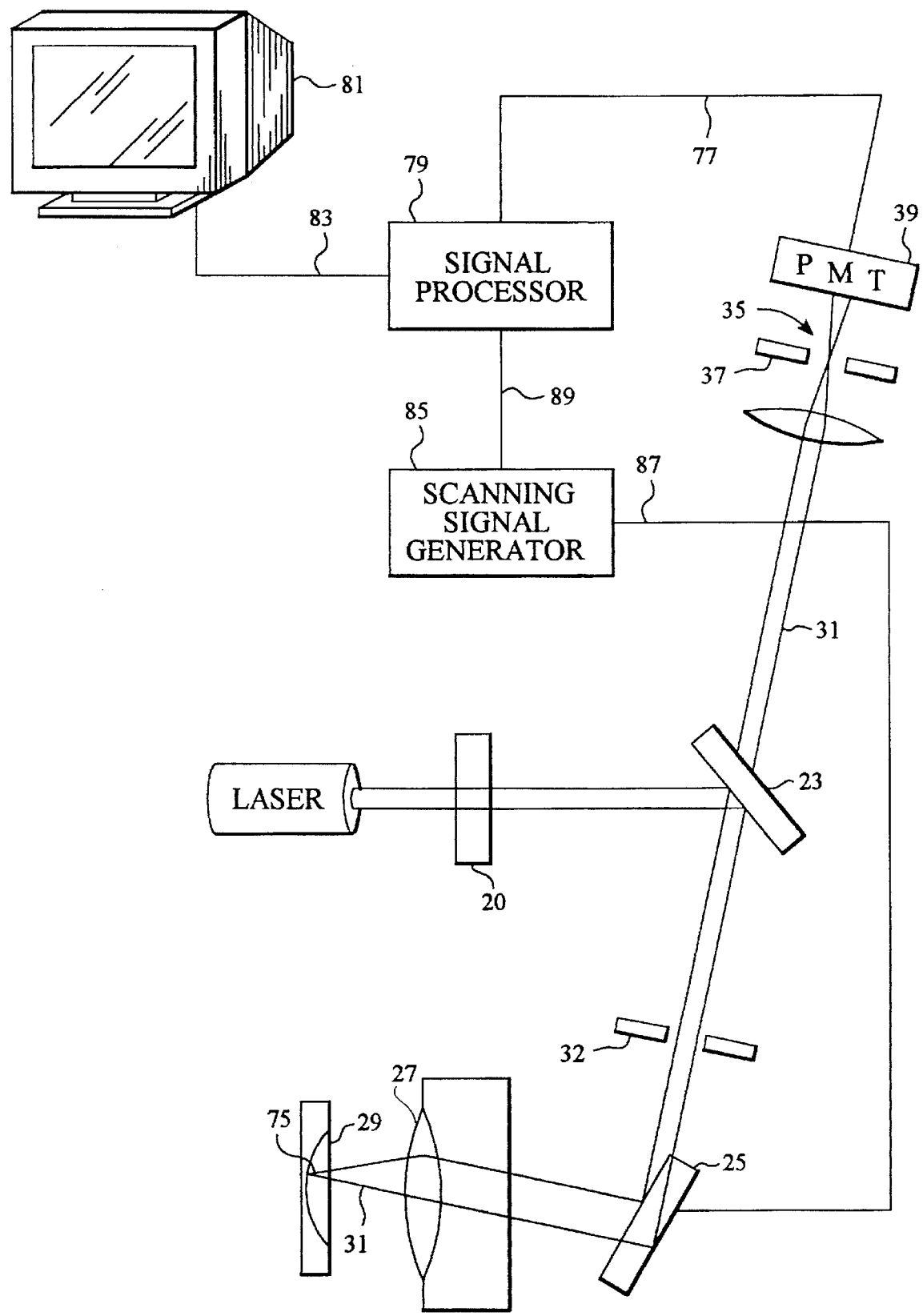
FIG. 9 is a simplified side view of the optical components shown on FIG. 2 including a video display system to reproduce an image of the sample in accordance with the present invention.

Referring to FIG. 9, the operation of the system is discussed. Preferably, the system is to take advantage of detection using the conjugate focal (confocal) technique. In this manner, retro-beam 31 is shown emanating from a point 75 which corresponds to a point source of light illuminated by an incident beam which was focused to a diffraction limited spot on sample 29. Retro-beam 31 is imaged on detector 39, after passing through aperture 35. Aperture 35, in spatial filter 37, isolates the detection of the system to that substantially coincident with the illuminating spot so that aperture 35 and point 75 are optically conjugated with each other. Although any light detector may be used, it is preferred to use a photomultiplier tube. The signal from the photomultiplier tube passes through electrical connections 77 to a signal processor 79 of a video display system including a video display screen 81. The signal from the photomultiplier tube 39 modulates the intensity of the image signal transmitted from the processor 79 through the output line 83 to the display screen 81. A scanning signal generator 85, under control of the signal processor 79 via line 89, supplies electrical signals to the scanning apparatus 25 through electrical connections 87. The scanning apparatus 25 moves in response to the generator 85's signals. The signal from photomultiplier tube 39 is digitized and stored in memory and can be simultaneously scanned onto a display.

Although fluorescent confocal imaging is the preferred embodiment, the system may be used in a non-confocal manner. In this fashion, field stop 37 and aperture 35 may filter light in a either non-confocal or semi-confocal manner. In either manner, spatial filter 37 and aperture 35 improve the signal to noise ratio. Pupil stop 32 is configured to control the numerical aperture of the objective lens with respect to retro-beam 31. Without pupil stop 32, the numerical aperture at a given scan angle would be established by vignetting of objective lens 27. In effect, pupil stop 32 increases retro beam 31's intensity uniformity across objective lens 27's field of view and defines both the diameter of retro-beam 31 impinging upon focusing lens 33, and, therefore, the numerical aperture of the system. Although pupil stop 32 is shown positioned between scanning device 25 and beam splitter 23, pupil stop 32 may be positioned anywhere in the retro path between scanning device 25 and focusing lens 33.

An obvious extension of the system is in the area of reflection imaging. That is, the reflected laser beam could be collected at the detector instead of the fluorescent beam. Both the reflected beam and the fluorescent beam could be read at a different detector if a second dichroic beam splitter was positioned after the primary dichroic beam splitter. Or in a like manner, multiple fluorescent labels could be detected by using multiple secondary beam splitters and detectors.

Figure 10:
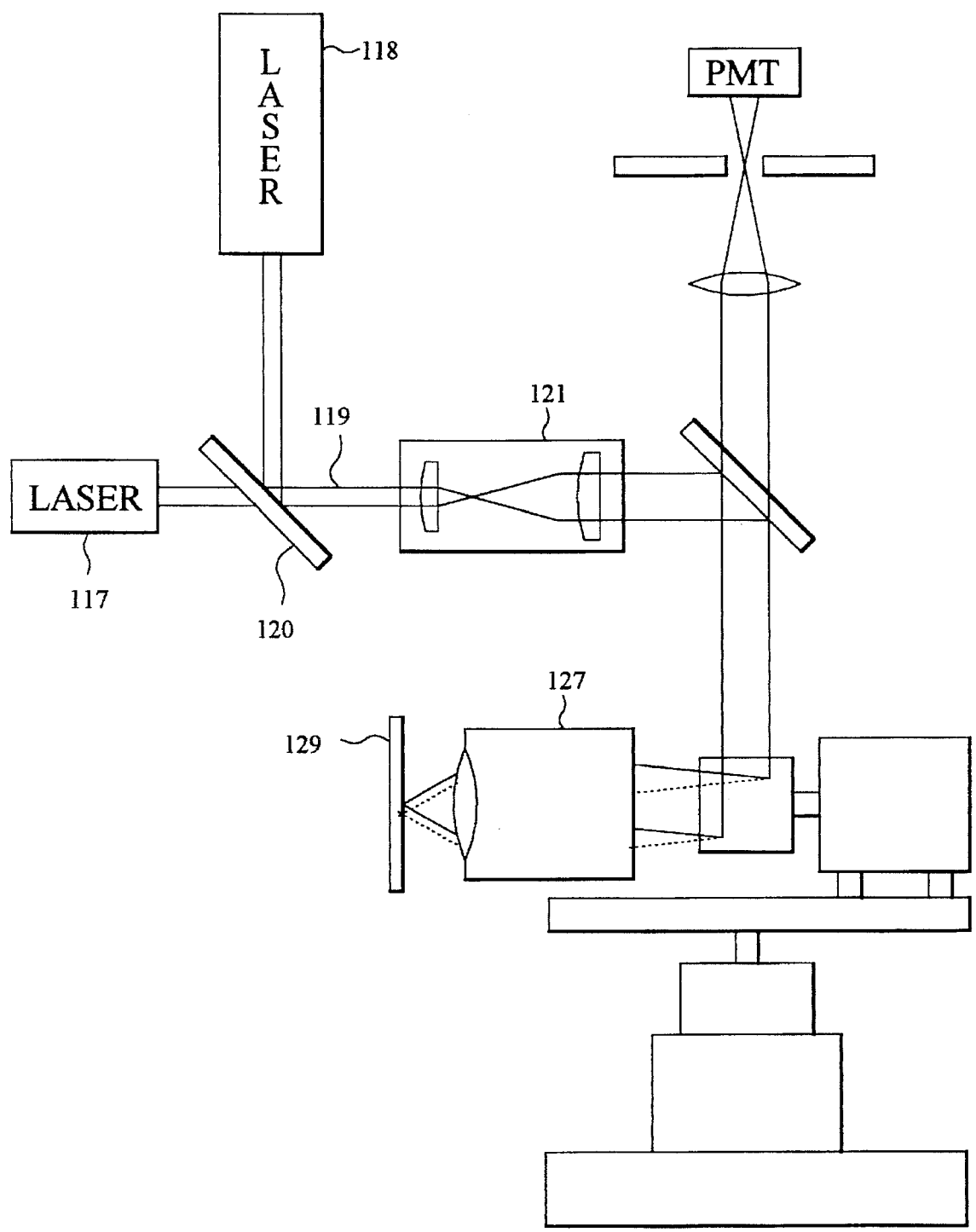
FIG. 10 is a side view of the invention shown in FIG. 2 in accord with an alternate embodiment.

Referring to FIG. 10, a second embodiment of the present invention is shown in which a further benefit of having all axial chromatic aberrations corrected in the retro-path is described. The second embodiment of the system includes all of the features of the systems described above with respect to FIG. 1, except two or more light sources 117 and 118 are provided, each of which emits a wavelength different from the remaining light source, forming an incident beam 119 comprising multi-chromatic light. The light sources may be utilized simultaneously, or each could be scanned individually by turning-off, or shuttering, the undesired light source. A beam expander 121 is optically coupled to at least one of the light sources 117 and 118 to control the collimated beam diameter and to correct for any axial chromatic aberrations in the system along the incident beam 119 path. In this fashion, substantially all light comprising incident beam 119 will impinge upon the same focal plane of sample 129. This is particularly useful for providing a highly efficient confocal imaging system.

Each light source 117 and 118 may be uniquely associated with a beam expander. It is preferred, however, that all light sources are in optical communication with a common beam expander, as shown, in order to reduce both the size and cost of the system. To that end, a dichroic filter 120 is disposed between light sources 117 and 118 and beam expander 121. Dichroic filter 120 allows light from source 117 to pass through while reflecting light from source 118 so that the light from both form incident beam 119 before entering beam expander 121. Beam expander 121 has optical properties that introduce axial chromatic aberrations to cancel axial chromatic aberrations introduced by optical elements, e.g., objective lens 127 in the system following beam expander 121 to ensure all wavelengths of light comprising beam 119 impinge upon the same focal plane of sample 129.

Figure 11:
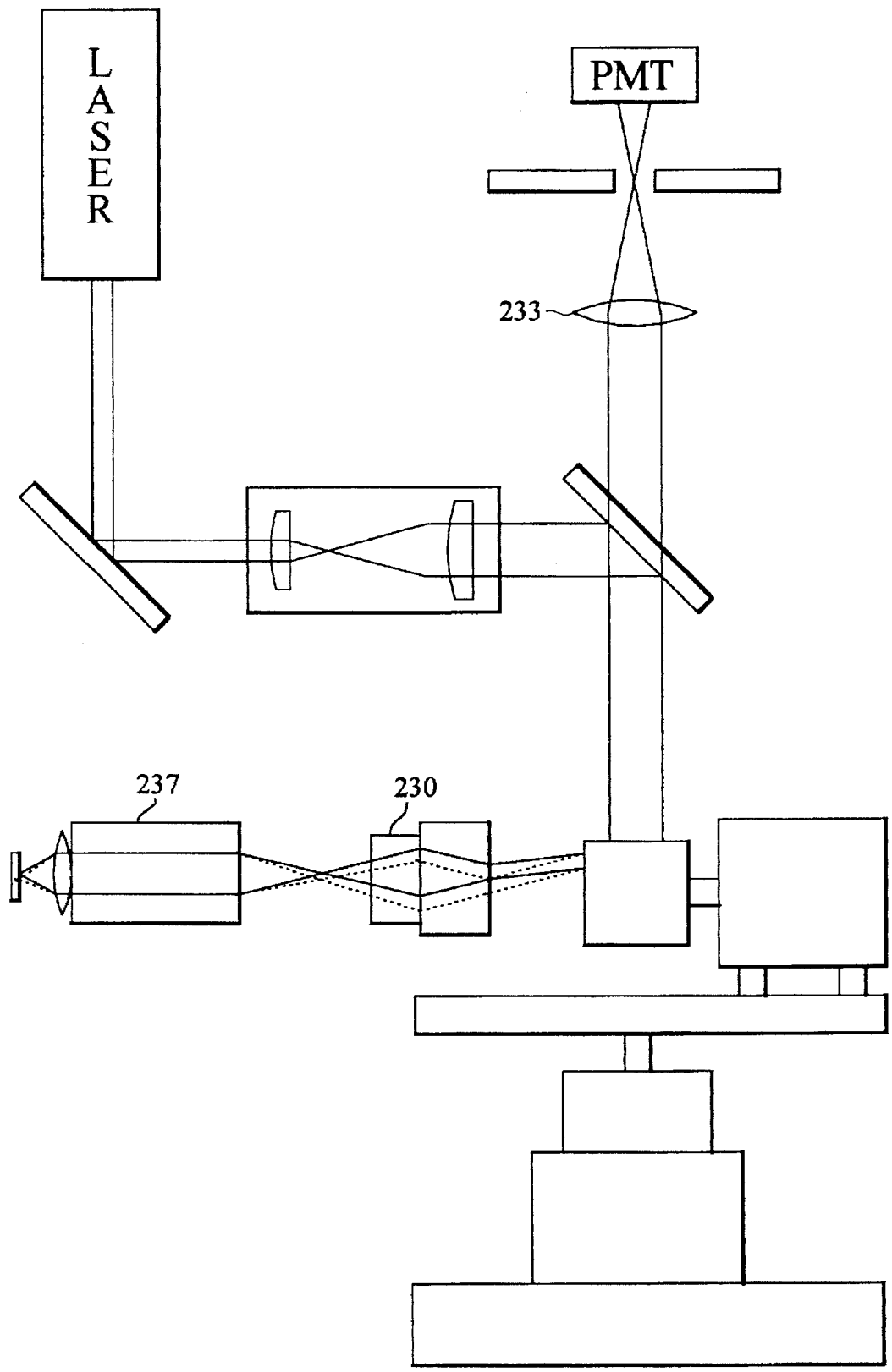
FIG. 11 is a side view of an alternate embodiment of the present invention.

Referring to FIG. 11, shown is another objective lens system that may be employed by having all axial chromatic aberrations corrected in the retro-path. The collection lens 233 may be used in a microscope style system. In such a system, objective lens 227 is optically coupled to reflecting element 243 via an eye piece 230. The remaining elements of the system are identical to those shown in FIG. 2.

We claim:

1. An optical scanning system comprising:
   an objective defining an optical axis and a field of view, said objective positioned proximate to the sample to receive an incident beam of light and directing said beam onto the sample, producing an illuminated spot thereon with said objective collecting light emitted from said spot and forming a retro-beam, said objective having optical properties to provide a substantially uniform detection sensitivity across said field of view by introducing into said system a specified amount of axial chromatic aberrations while reducing lateral chromatic aberrations;

a beam source for emitting said incident beam;

means, in said optical axis, for scanning said spot, on said sample surface;

a detector;

a spatial filter, positioned proximate to said detector, having a substantially transmissive aperture, restricting light scattered rearwardly to increase signal response;

a focusing lens means, disposed in the path of said retro-beam, for directing said retro-beam onto said aperture, said focusing lens means having optical properties to compensate for axial chromatic aberrations introduced by said objective; and means, positioned in said optical axis between said beam source and said objective, for separating said incident beam from said retro-beam, wherein said objective directs said retro-beam onto said separating means with said separating means directing said retro-beam through said aperture and onto said detector.

2. The optical scanning system of claim 1 further including a pupil stop positioned in a path of said retro-beam between said scanning means and said spatial filter, with said pupil stop defining a diameter of said retro-beam.

3. The optical scanning system of claim 1 wherein said beam source includes a plurality of light sources each of which is in optical communication with a beam expander, with said plurality of light sources emitting differing wavelengths providing said incident beam with multiple wavelengths of lights, said beam expander having optical properties to compensate for axial chromatic aberrations in said system, thereby ensuring substantially all of said light in said beam impinges upon a common focal plane of said sample.

4. The optical scanning system of claim 1 wherein said spatial filter restricts light scattered rearwardly in a semi-confocal manner, with a diameter of said aperture being larger than a diameter of said spot.

5. The optical scanning system of claim 1 wherein said retro-beam includes fluorescent light.

6. The optical scanning system of claim 1 wherein said objective defines an external entrance pupil sufficiently distant from the objective to be positioned proximate to a scanning device.

7. The optical scanning system of claim 1 wherein said objective is telecentric in object space.

8. The optical scanning system of claim 1 wherein said scanning means raster scans said spot over the entire area of said sample.

9. The optical scanning system of claim 1 further including means, connected to said detector, for displaying a visual image of said sample.

10. The optical scanning system of claim 1 wherein a diameter of said aperture is equal to a diameter of said spot, forming a confocal system.

11. The optical scanning system of claim 1 further including means, positioned between said beam source and said separating means, for changing the diameter of said incident beam.

12. The optical scanning system of claim 1 wherein said retro-beam comprises of substantially all light reflected rearwardly from said surface.

13. The optical scanning system of claim 12 wherein said scanning means includes a reflective surface positioned at the pupil of the system.

14. An optical scanning system comprising:

an objective defining an optical axis and a field of view, said objective positioned proximate to the sample to receive an incident beam of light and directing said beam onto the sample, producing an illuminated spot thereon with said objective collecting light emitted from said spot and forming a retro-beam, said objective having optical properties to provide a substantially uniform detection sensitivity across said field of view by introducing into said system a specified amount of axial chromatic aberrations while reducing lateral chromatic aberrations;

a beam source for emitting said incident beam;

means, in said optical axis, for scanning said spot, on said sample surface;

a detector;

a spatial filter, positioned proximate to said detector, having a substantially transmissive aperture, restricting light scattered rearwardly to increase signal response;

a focusing lens means, disposed in the path of said retro-beam, for directing said retro-beam onto said aperture;

means, positioned in said optical axis between said beam source and said objective, for separating said incident beam from said retro-beam, wherein said objective directs said retro-beam onto said separating means with said separating means directing said retro-beam through said aperture and onto said detector;

a pinhole; and a lens positioned to collimate light passing through said pinhole, with said pinhole disposed between said beam source and said separating means, and said collimating lens disposed between said separating means and said pinhole, wherein said beam source is a non-coherent source of light optically focused on said pinhole.

15. The optical scanning system of claim 14 wherein said beam source comprises a light emitting diode.

16. The optical scanning system of claim 14 wherein said spatial filter restricts light scattered rearwardly in a confocal manner.

17. The optical scanning system of claim 14 wherein said retro-beam includes fluorescent light.

18. The optical scanning system of claim 14 further including a beam expander, wherein said beam source includes a plurality of light sources each of which is in optical communication with said beam expander, with said plurality of light sources emitting differing wavelengths providing said incident beam with multiple wavelengths of light, said beam expander having optical properties to compensate for axial chromatic aberrations present in said system, thereby ensuring substantially all of said light in said beam impinges upon a common focal plane of said sample.

19. The optical scanning system of claim 14 wherein said objective is telecentric in object space.

20. The optical scanning system of claim 14 wherein said scanning means includes a reflective surface positioned at the pupil of the system.

21. The optical scanning system of claim 14 wherein said focusing lens means has optical properties to compensate for axial chromatic aberrations introduced by said objective.

22. An optical scanning system comprising:

an objective defining an optical axis and a field of view, said objective positioned proximate to the sample to receive an incident beam of light and directing said beam onto the sample, producing an illuminated spot thereon with said objective collecting light emitted from said spot and forming a retro-beam, said objective having optical properties to provide a substantially uniform detection sensitivity across said field of view by introducing into said system a specified amount of axial chromatic aberrations while reducing lateral chromatic aberrations;

a beam source for emitting said incident beam;

means, in said optical axis, for scanning said spot, on said sample surface;

a detector;

a spatial filter, positioned proximate to said detector, having a substantially transmissive aperture, restricting light scattered rearwardly to increase signal response;

a focusing lens means, disposed in the path of said retro-beam, for directing said retro-beam onto said aperture; and means, positioned in said optical axis between said beam source and said objective, for separating said incident beam from said retro-beam, said separating means including a mirror having a diameter greater than the diameter of said incident beam and smaller than the diameter of said retro-beam, with the diameter of the retro-beam being substantially larger than the diameter of the incident beam, wherein said objective directs said retro-beam onto said separating means with said separating means directing said retro-beam through said aperture and onto said detector.

23. The optical scanning system of claim 22 wherein said spatial filter restricts light scattered rearwardly in a confocal manner.

24. The optical scanning system of claim 22 wherein said retro-beam includes fluorescent light.

25. The optical scanning system of claim 22 further including a beam expander, wherein said beam source includes a plurality of light sources each of which is in optical communication with said beam expander, with said plurality of light sources emitting differing wavelengths providing said incident beam with multiple wavelengths of light, said beam expander having optical properties to compensate for axial chromatic aberrations present in said system, thereby ensuring substantially all of said light in said beam impinges upon a common focal plane of said sample.

26. The optical scanning system of claim 22 wherein said objective is telecentric in object space.

27. The optical scanning system of claim 22, further including a pinhole and a lens positioned to collimate light passing through said pinhole, with said pinhole disposed between said beam source and said separating means, and said collimating lens disposed between said separating means and said pinhole, wherein said beam source is a non-coherent source of light optically focused on said pinhole.

28. The optical scanning system of claim 22 wherein said scanning means includes a reflective surface positioned at the pupil of the system.

29. An optical scanning system comprising:

an optical defining an optical axis and a field of view, said objective positioned to receive an incident beam of light and directing said beam onto the sample, producing an illuminated spot thereon with said objective collecting light emitted from said spot and forming a retro-beam, said objective having optical properties to provide a substantially uniform detection sensitivity across said field of view by allowing a specified amount of axial chromatic aberrations while decreasing lateral chromatic aberrations;

a beam source for emitting said incident beam;

means, in said optical axis, for scanning said spot, on said sample surface;

a detector;

a spatial filter, positioned proximate to said detector, having a substantially transmissive aperture, restricting light scattered rearwardly to decrease background noise at the detector;

a focusing lens means, disposed in the path of said retro-beam, for directing said retro-beam onto said aperture, said focusing lens having optical properties to compensate for axial chromatic aberrations allowed by said objective;

means positioned in said optical axis between said beam source and said objective for separating said incident beam from said retro-beam, wherein said objective directs said retro-beam onto said separating means with said separating means directing said retro-beam through said aperture and onto said detector.

30. The optical scanning system of claim 29 further including a pupil stop positioned in a path of said retro-beam between said scanning means and said spatial filter, with said pupil stop defining a diameter of said retro-beam.

31. The optical scanning system of claim 30 wherein said spatial filter restricts light scattered rearwardly in a confocal manner.

32. The optical scanning system of claim 31 wherein said retro-beam includes fluorescent light.

33. The optical scanning system of claim 32 wherein said beam source includes a plurality of light sources each of which is in optical communication with a beam expander, with said plurality of light sources emitting differing wavelengths providing said incident beam with multiple wavelengths of light, said beam expander having optical properties to compensate for axial chromatic aberrations present in said system, thereby ensuring substantially all of said light in said beam impinges upon a common focal plane of said sample.

34. The optical scanning system of claim 33 wherein said objective is telecentric in object space.

35. The optical scanning system of claim 34 wherein said separating means is a mirror having a diameter greater than the diameter of said incident beam and smaller than the diameter of said retro-beam, with the diameter of the retro-beam being substantially larger than the diameter of the incident beam.

36. The optical scanning system of claim 35 wherein said incident beam is collimated and said emitted light is reflected light.

37. An optical scanning system comprising:

an objective defining an optical axis and a field of view, said objective positioned to receive an incident beam of light and directing said beam onto the sample, producing an illuminated spot thereon with said objective collecting light emitted from said spot and forming a retro-beam, said objective having optical properties to provide a substantially uniform detection sensitivity across said field of view by introducing a specified amount of axial chromatic aberrations to optimize the lens for lateral chromatic aberrations while reducing lateral chromatic aberrations to improve detection sensitivity in said field of view;

a plurality of light sources emitting differing wavelengths providing said incident beam with multiple wavelength lights, each of which is in optical communication with a beam expander in optical communication with each of said plurality of light sources, said beam expander having optical properties to compensate for axial chromatic aberrations introduced by said objective, thereby ensuring substantially all of said light in said beam impinges upon a common focal plane of said sample;

means, in said optical axis, for scanning said spot, on said sample surface, said scanning means including a reflective surface;

a detector;

a spatial filter, positioned proximate to said detector, having a substantially transmissive aperture, restricting light scattered rearwardly to increase signal response;

a focusing lens means, disposed in the path of said retro-beam, for directing said retro-beam onto said aperture, said focusing lens having optical properties to compensate for axial chromatic aberrations introduced by said objective; and means positioned in said optical axis between said beam source and said objective for separating said incident beam from said retro-beam, wherein said objective directs said retro-beam onto said separating means with said separating means directing said retro-beam through said aperture and onto said detector.

38. The optical scanning system of claim 37 further including a pupil stop positioned in a path of said retro-beam, between said scanning means and said collector lens means, with said pupil stop defining a diameter of said retro-beam.

39. The optical scanning system of claim 38 wherein said aperture defines a diameter equal to a diameter of said spot, thereby optimizing confocal imaging of said sample.

40. The optical scanning system of claim 39 further including means, connected to said detector, for displaying a visual image of said sample.

41. The optical scanning system of claim 40 wherein said scanning means raster scans said spot over the entire surface of said sample.

42. The optical scanning system of claim 41 wherein said scanning means includes a reflective surface positioned at an entrance pupil of said objective.

* * * * *

UNITED STATES PATENT AND TRADEMARK OFFICE
CERTIFICATE OF CORRECTION

PATENT NO. : 5,646,411
DATED : July 8, 1997
INVENTOR(S) : Robert C. Kain et al.

It is certified that error appears in the above-indentified patent and that said Letters Patent is hereby corrected as shown below:

Claim 29, column 11, line 54, "an optical defining an optical axis" should read -- an objective defining an optical axis --.

Signed and Sealed this

Seventh Day of October, 1997

*Attest:*

BRUCE LEHMAN

*Attesting Officer*      *Commissioner of Patents and Trademarks*